United States Patent
Sutton

(10) Patent No.: US 6,529,779 B1
(45) Date of Patent: Mar. 4, 2003

(54) INFLATABLE ELECTRODE FOR TEMPORARY PACING

(75) Inventor: Richard Sutton, London (GB)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/719,438
(22) PCT Filed: Jun. 9, 1999
(86) PCT No.: PCT/SE99/01015
§ 371 (c)(1), (2), (4) Date: Dec. 11, 2000
(87) PCT Pub. No.: WO99/64104
PCT Pub. Date: Dec. 16, 1999

(30) Foreign Application Priority Data

Jun. 12, 1998 (SE) .............................................. 9802104

(51) Int. Cl.[7] ......................... A61B 5/0408; A61N 1/05
(52) U.S. Cl. ...................... 607/126; 600/375; 600/470; 606/41
(58) Field of Search ............................. 607/4, 5, 9, 98, 607/99, 119, 122, 123, 126, 128, 148; 606/41; 600/374, 375, 381, 467, 470

(56) References Cited

U.S. PATENT DOCUMENTS

| 5,170,802 A | | 12/1992 | Mehra | 607/126 |
|---|---|---|---|---|
| 5,356,427 A | * | 10/1994 | Miyata et al. | 607/122 |
| 5,411,546 A | | 5/1995 | Bowald et al. | 607/126 |
| 5,431,683 A | | 7/1995 | Bowald et al. | 607/5 |
| 5,697,965 A | | 12/1997 | Griffin, III | 607/123 |
| 5,860,974 A | * | 1/1999 | Abele | 607/122 |
| 6,004,269 A | * | 12/1999 | Crowley et al. | 607/122 |

FOREIGN PATENT DOCUMENTS

WO   WO 94/07564   4/1994

* cited by examiner

Primary Examiner—Willis R. Wolfe
(74) Attorney, Agent, or Firm—Schiff Hardin & Waite

(57) ABSTRACT

A temporary balloon-type electrode for insertion and temporary fixation in a blood vessel of a heart, for determining a suitable place therein for a subsequently inserted and fixed permanent electrode, has a catheter and an inflatable and deflatable balloon member disposed at a distal end portion of the catheter. The balloon member has at least one radially expandable hollow body. At least one electrode surface contact member is disposed at a peripheral portion of the hollow body, and flow passages are provided for allowing a blood flow to pass the balloon member when inflated. The temporary balloon-type electrode is particularly suited for use in coronary sinus and peripheral coronary veins of the heart.

17 Claims, 1 Drawing Sheet

INFLATABLE ELECTRODE FOR TEMPORARY PACING

BACKGROUND OF THE INVENTION

1. Field of the Invention

The present invention relates in general to a balloon-type electrode to be inserted into a blood vessel of a heart. More particularly, the present invention relates to a temporary balloon-type electrode adapted for insertion and temporary location in a blood vessel of a heart for determining a suitable place therein for a subsequently inserted and fixated permanent electrode.

2. Description of the Prior Art

When carrying out transvenous heart pacing, in particular transvenous pacing of the left atrium and left ventricle of the heart for achieving a desired coordination of left and right ventricular contraction patterns, a very accurate location of the heart stimulation electrode in coronary sinus or in a peripheral vein is necessary. The stimulation electrode used for this purpose needs to be radially expandable into a fix contact with the interior surface of the blood vessel in question, and it must have a structural configuration which does not obstruct or affect the blood flow through the electrode in any deteriorating manner.

Defibrillation electrodes are known for intravascular implantation in coronary vessels of the heart for delivering defibrillation pulses thereto. For example U.S. Pat. No. 5,170,802 discloses such a radially expandable defibrillation electrode which is initially mounted around an expandable portion of a balloon catheter which is guided by a guide catheter to a desired location for implantation of the electrode. Upon the guide catheter reaching a position adjacent the desired location for implantation, the balloon catheter is advanced out of the distal end of the guide catheter and brought into contact with the inner wall of the blood vessel by inflating the balloon portion, thereby causing the electrode to be permanently deformed by straightening of the zigzag bands thereof so as to remain in contact with the interior of the blood vessel after deflation of the expandable portion of the balloon catheter. The electrode provides an elongated conductive surface in the general form of a hollow cylinder which allows the implantation of a large surface area electrode which may be useful for defibrillation, cardioversion or other stimulation without substantially impeding the flow of blood through the blood vessel. The electrode may also take the form of a so-called resilient stent which by itself may expand radially into contact with the inner wall of the blood vessel when exiting a distal end opening of the guide catheter. Similar prior art solutions are disclosed in e.g. U.S. Pat. Nos. 5,411,546 and 5,431,683.

Once fixed to the interior surface of a blood vessel such prior art electrodes are not easily removable from the implantation site which makes them unsuitable for sensing activities for determining the best pacing/sensing position in the blood vessel for transvenous left-heart pacing/sensing before a stimulation electrode is fixated.

SUMMARY OF THE INVENTION

It is an object of the present invention to provide a temporary balloon-type electrode wherein the aforementioned drawbacks of the prior art electrodes are avoided and which is suitable for insertion and temporary location in a blood vessel of a heart for determining by a sensing or mapping procedure an appropriate place therein for a subsequently inserted and fixated, secondary stimulation electrode.

This object is achieved by a balloon-type electrode of the type initially described which has a catheter having a distal end portion and a proximal end portion, an inflatable and deflatable balloon member located at the distal end portion of the catheter and having at least one radially expandable hollow body; at least one electrode surface contact member disposed at a peripheral portion of the hollow body, and flow passages allowing a blood flow to pass the balloon member when inflated.

The inventive electrode has thus a structure which allows a temporary insertion thereof into blood vessels of the heart, such as coronary sinus or peripheral coronary veins, by means of a suitable guide wire or stylet and a subsequent inflation of the or each radially expandable hollow balloon body so as to bring each electrode surface contact member into contact with the interior surface of the blood vessel. In this state, when determining the best position for subsequent transvenous pacing, various criteria need to be fulfilled.

1) The hemodynamic criteria:
   a) The position must be determined to optimize the hemodynamical performance of the heart which can be achieved through ECG-analyses to determine that the intended left/right ventricle activation is obtained.
   b) Alternatively, this can be determined through ultrasound measurement, which provides a more precise information of the hemodynamnic situation.
   c) Left/right blood-pressure curves may also provide valuable information on the hemodynamic situation.

2) Sensing criteria:
   The sensing signal must be of acceptable amplitude, typically >2 mV.

3) Threshold criteria:
   The pacing threshold must allow continuous pacing with acceptable energy consumption. The required threshold is in the order of 2 V.

4) Other criteria:
   Respiratory stability
   QRS-activation pattern
   QRS-duration In the process of finding the most appropriate location for transvenous left-heart stimulation the position of the temporary balloon electrode may be varied by deflating the balloon body, displacing the balloon electrode on the guide wire, and reinflating it at another position where the above-mentioned criteria are again determined and compared. During this temporary fixation and temporary stimulation by means of the balloon-type electrode, the flow passages formed therein ensure sufficient blood flow to pass the balloon member. When good values of these criteria have been obtained for the intended heart stimulation activities, the temporary balloon electrode is removed by sliding it off the guide wire which remains in situ. The exact position for the best heart stimulation may be observed by X-ray fluoroscopy with the help of markers on the remaining guide wire and/or on the balloon electrode. Then the balloon electrode may be replaced by a secondary, permanent stent-type electrode which is guided by the guide wire to the preselected stimulation position and affixed to the interior surface of the blood vessel at that position by a radial expansion of the stent electrode. Finally, the guide wire is removed.

Further features and advantages of the balloon-type electrode of the present invention will be apparent from the following detailed description of the invention in conjunction with the accompanying drawings.

DESCRIPTION OF PREFERRED EMBODIMENTS

Figure 1:
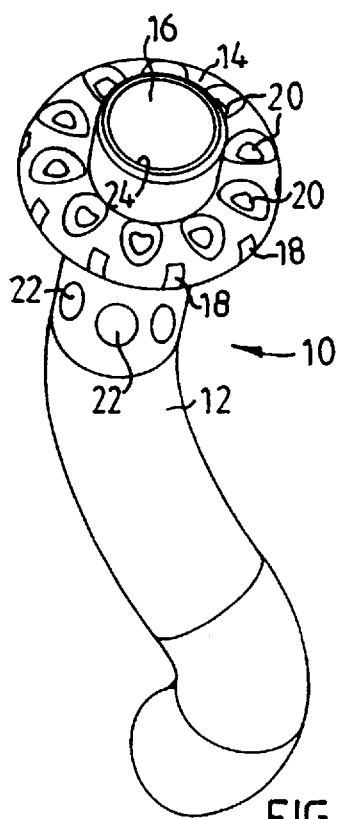
FIG. 1 is a perspective view of a first embodiment of a balloon-type electrode of the present invention.

A distal end portion of a balloon-type electrode 10 for temporary fixation in a blood vessel of a patient's heart is shown in FIG. 1. The electrode 10 comprises an elongated catheter 12 and an inflatable and deflatable balloon member 14 located at the distal end portion of the catheter 12. The catheter 12 defines a central lumen 16 for receiving a guide wire or stylet. The balloon member 14 is formed as an annular or ring-shaped hollow body which may be inflated by a suitable liquid, such as a solution of NaCl, so as to expand radially into contact with the inner wall of a heart blood vessel, in particular coronary sinus, or even further to peripheral veins of the heart.

At the outer periphery of the ring-shaped body 14 there are disposed a plurality of discrete electrode surface contact members 18 which are evenly distributed around the circumference of the body 14 for making proper electrical contact with the inner wall of the blood vessel in question. The electrode surface contact members 18 may be connected in parallel or individually to an associated, external measuring device (PSA) (not shown) through leads (not shown) running internally or externally of the catheter 12. Individually connectable surface contact members 18 would make it possible to determine the angular position, i.e. the X and Y-coordinates, of the most favourable surface contact member(s) for pacing.

In order to allow for an appropriate blood flow past an inflated, temporarily fixated balloon member 14 against the inner wall of the blood vessel at a potential stimulation site therein, a plurality of axial and circumferentially separated flow passages in the form of holes are formed in the ring-shaped balloon member 14. A plurality of circumferentially separated radial holes 22 may also be formed in the wall of the catheter 12 just downstream of the balloon member 14, i.e. on the proximal side thereof, to allow blood to flow from the upstream side of the balloon member 14 to the downstream side thereof via an opening 24 at the distal end of the catheter 12 and the holes 20 and/or 22.

Figure 2:
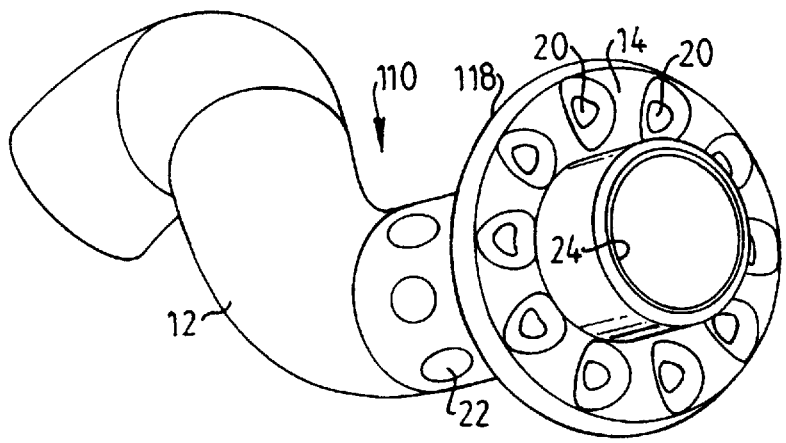
FIG. 2 is a perspective view of a second embodiment of a balloon-type electrode of the present invention.

A second embodiment of a temporary balloon electrode 110 of the present invention shown in FIG. 2 differs from the first embodiment in FIG. 1 only in that the plurality of electrode surface contact members 18 have been replaced by a single ring-shaped contact member 118, which is made collapsible to facilitate insertion of the balloon electrode 110 in the deflated condition thereof. To this end the ring-shaped contact member 118 may consist of an expandable annular coil spring element or the like.

Figure 3:
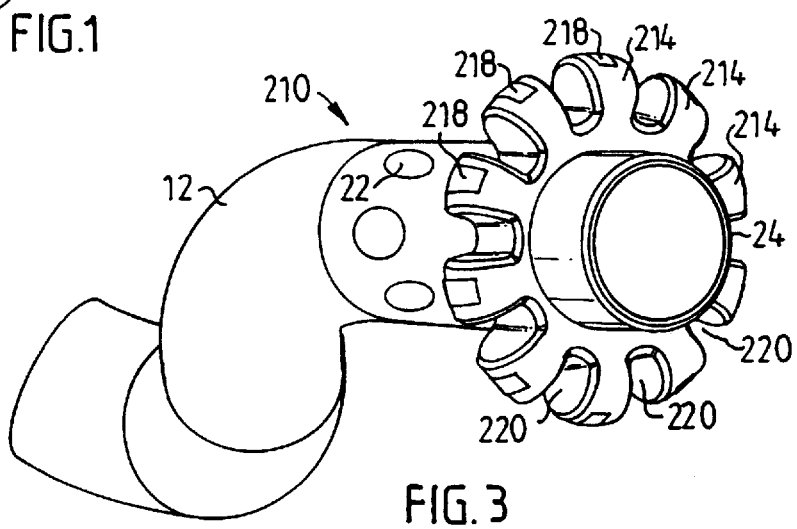
FIG. 3 is a perspective view of a third embodiment of a balloon-type electrode of the present invention.

A third embodiment of a temporary balloon electrode 210 according to the present invention is illustrated in FIG. 3. In this embodiment the balloon member has a plurality of radially expandable hollow sections 214, which define blood flow passages 220 between the adjacent sections 214. Supplemental blood flow bypass holes 22 may also be arranged in the catheter downstream of the balloon member 210. Individual electrode surface contact members 218 are located at the tip of the radially expandable sections 214 and may—like in the first embodiment—be connected in parallel or individually to an external PSA through leads (not shown).

Figure 4:
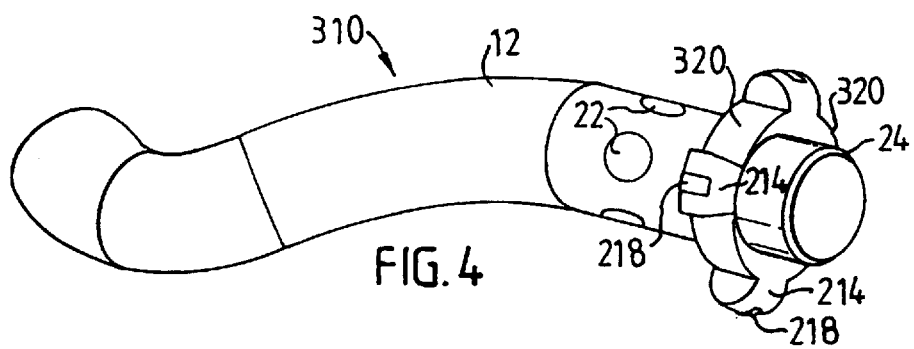
FIG. 4 is a perspective view of a fourth embodiment of a balloon-type electrode of the present invention.

FIG. 4 illustrates a fourth embodiment of a balloon-type electrode 310, which differs from the third one in FIG. 3 only in that there are only four radially expandable hollow sections 214. This results in wider blood flow passages 320 between adjacent expanded sections 214.

In all four embodiments of the balloon electrode of the present invention the balloon member may consist of latex and have a diameter in the approximate range of 2.5–20 mm in the inflated condition and an axial length of approximately 2.5 mm. X-ray markers, e.g. a layer of lead or tantalum, may be provided on the catheter 12, e.g. on each side of the balloon member 14;214 to indicate a proper electrode position for a later inserted, permanent electrode stent for pacing or other stimulation or sensing purposes. Alternatively, the guide wire used for the positioning of the balloon electrode may be provided with X-ray markers to indicate the selected position for the electrode stent. The distal end of the catheter 12 defining the opening 24 should have a rounded front in order to achieve a smooth passage through a blood vessel during the insertion of the catheter.

Thus, the temporary balloon electrode of the present invention is used as a position finder for a later inserted and fixed permanent electrode stent. In finding a proper position for the electrode stent in coronary sinus, which is a suitable place for transvenous pacing of both the left atrium and left ventricle, the balloon electrode 10; 110;210 is inserted and guided to a potential stimulation position therein by a guide wire or stylet (not shown) located in the lumen 16 of the catheter 12. Then, when reaching a possible appropriate stimulation position, the balloon member is inflated into contact with the inner wall of the blood vessel for assessment of various electrical and hemodynamic parameters for obtaining appropriate transvenous pacing, such as good electrogram, threshold, respiratory stability, QRS-activation pattern and duration etc. If such appropriate criteria are not obtained, the balloon electrode is deflated and displaced to another location and again inflated for further measurements. In the inflated condition of the balloon electrode a sufficient flow of blood may be established past the balloon member with the help of the flow passages 20;22,222,24. Once a proper position for transvenous pacing or stimulation has been found, this position is observed by means of X-ray technology sensing the X-ray markers on the catheter and/or guide wire and stored. The balloon electrode is then deflated and withdrawn from the patient while the guide wire remains in situ. A secondary, permanent stent-type electrode (not shown) is thereafter guided by the guide wire to the preselected stimulation position and fixed to the inner wall of the vessel at that position by a radial self-expansion of the electrode stent. After the fixation of the electrode stent the guide wire is removed.

Although modification and changes may be suggested by those skilled in the art, it is the intention of the inventor to embody within the patent warranted hereon all changes and modifications as reasonably and properly come within the scope of his contribution to the art.

What is claimed is:

1. A temporary balloon-type electrode adapted for insertion and temporary location in a blood vessel of a heart for determining a suitable place therein for a subsequently inserted and fixed permanent electrode, said temporary electrode comprising:

a catheter having a distal end portion and a proximal end portion;

an inflatable and deflatable balloon disposed at said distal end portion of the catheter and having at least one radially expandable hollow body;

at least one electrode surface contact member disposed at a peripheral portion of said hollow body; and flow passages allowing a blood flow to pass the balloon member when inflated.

2. A balloon-type electrode as claimed in claim 1 wherein said at least one electrode surface contact member is a single ring-shaped electrode surface contact member disposed at the peripheral portion of said hollow body.

3. A balloon-type electrode as claimed in claim 1 wherein said hollow body has an axial length of approximately 2–5 mm.

4. A balloon-type electrode as claimed in claim 1 wherein said hollow body has a diameter in a range between about 2.5 mm and about 20 mm when inflated.

5. A balloon-type electrode as claimed in claim 1 wherein the distal end portion of the catheter has a rounded central opening.

6. A balloon-type electrode as claimed in claim 1 wherein the balloon member is comprised of latex.

7. A balloon-type electrode as claimed in claim 1 comprising X-ray markers disposed on the distal and proximal side of the hollow body.

8. A balloon-type electrode as claimed in claim 1, wherein said radially expandable body comprises a plurality of hollow sections.

9. A balloon-type electrode as claimed in claim 8, wherein said flow passages are formed by spaces between adjacent pairs of said hollow sections.

10. A balloon-type electrode as claimed in claim 1 wherein said peripheral portion of said hollow body has a substantially convex profile, as seen in an axial cross-sectional view through said hollow body.

11. A balloon-type electrode as claimed in claim 10, wherein said at least one electrode surface contact member has a convex profile, as seen in an axial cross-sectional view through said hollow body.

12. A balloon-type electrode as claimed in claim 1, wherein the radially expandable body is an annular hollow body.

13. A balloon-type electrode as claimed in claim 12, wherein said flow passages comprise a plurality of circumferentially separated holes extending axially through said annular hollow body.

14. A balloon-type electrode as claimed in claim 12, wherein said flow passages comprise holes in the catheter disposed adjacent and proximal to the radially expandable body.

15. A balloon-type electrode as claimed in claim 1 comprising a plurality of discrete electrode surface contact members circumferentially distributed along the peripheral portion of said hollow body.

16. A balloon-type electrode as claimed in claim 15, wherein said discrete electrode surface contact members are connectible in parallel.

17. A balloon-type electrode as claimed in claim 15, wherein said discrete electrode surface contact members are individually connected to an associated measuring device.

\* \* \* \* \*